United States Patent
Weber et al.

(10) Patent No.: US 8,702,691 B2
(45) Date of Patent: Apr. 22, 2014

(54) TREATMENT APPARATUS AND METHODS FOR DELIVERING ENERGY AT MULTIPLE SELECTABLE DEPTHS IN TISSUE

(75) Inventors: Bryan Weber, Livermore, CA (US); Richard Wyeth, Discovery Bay, CA (US)

(73) Assignee: Thermage, Inc., Hayward, CA (US)

( * ) Notice: Subject to any disclaimer, the term of this patent is extended or adjusted under 35 U.S.C. 154(b) by 791 days.

(21) Appl. No.: 11/423,068

(22) Filed: Jun. 8, 2006

(65) Prior Publication Data
US 2007/0088413 A1   Apr. 19, 2007

Related U.S. Application Data

(60) Provisional application No. 60/728,339, filed on Oct. 19, 2005.

(51) Int. Cl.
*A61B 18/12* (2006.01)
*A61B 18/14* (2006.01)
*A61B 18/00* (2006.01)

(52) U.S. Cl.
CPC ....... *A61B 18/14* (2013.01); *A61B 2013/00452* (2013.01); *A61B 2018/00738* (2013.01); *A61B 2018/0075* (2013.01); *A61B 2018/00958* (2013.01); *A61B 2018/124* (2013.01); *A61B 2018/1405* (2013.01); *A61B 2018/1467* (2013.01)
USPC ............................................. 606/34; 606/41

(58) Field of Classification Search
CPC .................. A61B 18/12; A61B 18/14; A61B 2018/00005; A61B 2018/00011; A61B 2018/0016; A61B 2018/00452; A61B 2018/00458; A61B 2018/00464; A61B 2018/0047; A61B 2018/00476; A61B 2018/00738; A61B 2018/0075; A61B 2018/00916; A61B 2018/00958; A61B 2018/124; A61B 2018/1405; A61B 2018/1467; A61B 2017/00747; A61B 2017/00752; A61B 2017/00756; A61B 2017/00761
USPC .................................. 606/41–42, 45, 48–50
See application file for complete search history.

(56) References Cited

U.S. PATENT DOCUMENTS

| | | | |
|---|---|---|---|
| 3,780,047 | A | 12/1973 | Gonser |
| 4,304,235 | A | 12/1981 | Kaufman |

(Continued)

FOREIGN PATENT DOCUMENTS

| | | |
|---|---|---|
| EP | 1685805 A1 | 8/2006 |
| WO | 9639087 A1 | 12/1996 |

(Continued)

OTHER PUBLICATIONS

Weber, Bryan, U.S. Appl. No. 11/470,041, filed Sep. 5, 2006.

(Continued)

*Primary Examiner* — Michael Peffley
*Assistant Examiner* — Samantha Good
(74) *Attorney, Agent, or Firm* — Wood, Herron & Evans LLP (57) ABSTRACT

Treatment apparatus and methods for delivering energy at multiple selectable tissue depths as selected by a clinician. The treatment apparatus includes at least two electrodes that are electrically isolated from each other, which permits each electrode to be independently energized for selecting different treatment depths. The electrodes may be concurrently energized with high frequency energy of the same polarity in a monopolar mode to deliver energy at a relatively deep depth into a patient's tissue, or with high frequency energy of a different polarity in a bipolar mode to provide a shallower penetration depth. Alternatively, the depth of energy delivery may be modified by energizing less than all of the electrodes. The electrodes may be energized with high frequency energy of different phase relationships to deliver energy concurrently in both monopolar and bipolar modes with the phase difference determining a depth of energy delivery.

6 Claims, 6 Drawing Sheets

(56) References Cited

U.S. PATENT DOCUMENTS

| | | |
|---|---|---|
| 4,658,819 A | 4/1987 | Harris et al. |
| 4,934,365 A | 6/1990 | Morgenthaler |
| 5,281,216 A | 1/1994 | Klicek |
| 5,487,759 A | 1/1996 | Bastyr et al. |
| 5,660,836 A | 8/1997 | Knowlton |
| 5,702,387 A * | 12/1997 | Arts et al. .................. 606/45 |
| 5,718,719 A | 2/1998 | Clare et al. |
| 5,755,753 A | 5/1998 | Knowlton |
| 5,849,020 A | 12/1998 | Long et al. |
| 5,871,524 A | 2/1999 | Knowlton |
| 5,919,219 A | 7/1999 | Knowlton |
| 5,948,011 A | 9/1999 | Knowlton |
| 6,148,232 A | 11/2000 | Avrahami |
| 6,241,753 B1 | 6/2001 | Knowlton |
| 6,293,941 B1 | 9/2001 | Strul et al. |
| 6,311,090 B1 | 10/2001 | Knowlton |
| 6,325,799 B1 | 12/2001 | Goble |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 * | 7/2002 | Stern .................. 606/41 |
| 6,423,057 B1 | 7/2002 | He et al. |
| 6,425,912 B1 | 7/2002 | Knowlton |
| 6,430,446 B1 | 8/2002 | Knowlton |
| 6,438,424 B1 | 8/2002 | Knowlton |
| 6,453,202 B1 | 9/2002 | Knowlton |
| 6,461,378 B1 | 10/2002 | Knowlton |
| 6,470,216 B1 | 10/2002 | Knowlton |
| 6,597,946 B2 | 7/2003 | Avrahami et al. |
| 6,611,706 B2 | 8/2003 | Avrahami et al. |
| 6,615,079 B1 | 9/2003 | Avrahami |
| 6,696,844 B2 | 2/2004 | Wong et al. |
| 6,708,060 B1 | 3/2004 | Avrahami et al. |
| 6,711,435 B2 | 3/2004 | Avrahami |
| 6,997,923 B2 | 2/2006 | Anderson et al. |
| 7,006,874 B2 | 2/2006 | Knowlton et al. |
| 7,022,121 B2 | 4/2006 | Stern et al. |
| 7,062,317 B2 | 6/2006 | Avrahami et al. |
| 7,094,215 B2 | 8/2006 | Davison et al. |
| 7,115,123 B2 | 10/2006 | Knowlton et al. |
| 7,123,957 B2 | 10/2006 | Avrahami |
| 7,141,049 B2 | 11/2006 | Stern et al. |
| 7,189,230 B2 | 3/2007 | Knowlton |
| D544,955 S | 6/2007 | Carson et al. |
| 7,229,436 B2 | 6/2007 | Stern et al. |
| 7,257,450 B2 | 8/2007 | Auth et al. |
| 7,267,675 B2 | 9/2007 | Stern et al. |
| 7,276,058 B2 | 10/2007 | Altshuler et al. |
| 7,278,991 B2 | 10/2007 | Morris et al. |
| 7,351,252 B2 | 4/2008 | Altshuler et al. |
| 7,422,586 B2 | 9/2008 | Morris et al. |
| 7,452,358 B2 | 11/2008 | Stern et al. |
| 7,473,251 B2 | 1/2009 | Knowlton et al. |
| 7,473,252 B2 | 1/2009 | Barry |
| 7,481,809 B2 | 1/2009 | Stern et al. |
| 7,494,488 B2 | 2/2009 | Weber |
| 2003/0139790 A1 | 7/2003 | Ingle et al. |
| 2003/0163178 A1 * | 8/2003 | Davison et al. .................. 607/101 |
| 2003/0199868 A1 * | 10/2003 | Desai et al. .................. 606/41 |
| 2003/0208152 A1 | 11/2003 | Avrahami et al. |
| 2003/0216719 A1 | 11/2003 | Debenedictis et al. |
| 2003/0236487 A1 | 12/2003 | Knowlton |
| 2004/0006339 A1 * | 1/2004 | Underwood et al. .................. 606/45 |
| 2004/0082940 A1 | 4/2004 | Black et al. |
| 2004/0111087 A1 | 6/2004 | Stern et al. |
| 2004/0116986 A1 | 6/2004 | Cantoni et al. |
| 2004/0210214 A1 | 10/2004 | Knowlton |
| 2004/0230227 A1 | 11/2004 | Avrahami et al. |
| 2005/0049582 A1 | 3/2005 | DeBenedictis et al. |
| 2005/0171582 A1 | 8/2005 | Matlock |
| 2005/0222555 A1 | 10/2005 | Manstein et al. |
| 2005/0222565 A1 | 10/2005 | Manstein |
| 2006/0004351 A1 | 1/2006 | Arless et al. |
| 2006/0015147 A1 | 1/2006 | Persson et al. |
| 2006/0047281 A1 | 3/2006 | Kreindel |
| 2006/0122668 A1 | 6/2006 | Anderson et al. |
| 2006/0206103 A1 | 9/2006 | Altshuler et al. |
| 2007/0078454 A1 | 4/2007 | McPherson |
| 2007/0078502 A1 | 4/2007 | Weber et al. |
| 2007/0083247 A1 | 4/2007 | Wyeth et al. |
| 2007/0093797 A1 | 4/2007 | Chan et al. |
| 2007/0093798 A1 | 4/2007 | DeBenedictis et al. |
| 2008/0058782 A1 | 3/2008 | Frangineas et al. |
| 2008/0082090 A1 | 4/2008 | Manstein |
| 2008/0287943 A1 | 11/2008 | Weber et al. |
| 2009/0012434 A1 | 1/2009 | Anderson |

FOREIGN PATENT DOCUMENTS

| | | |
|---|---|---|
| WO | 9724073 A1 | 7/1997 |
| WO | WO 99/12489 A2 | 3/1999 |
| WO | 9916502 | 4/1999 |
| WO | 0048644 A2 | 8/2000 |
| WO | 0053113 | 9/2000 |
| WO | 0100269 | 1/2001 |
| WO | 02053050 A1 | 7/2002 |
| WO | 03053266 | 3/2003 |
| WO | 03065915 | 8/2003 |
| WO | 03065915 A1 | 8/2003 |
| WO | 03065916 | 8/2003 |
| WO | 03086217 | 10/2003 |
| WO | 2004086943 | 10/2004 |
| WO | 2004087253 | 10/2004 |
| WO | 2004088700 | 10/2004 |
| WO | 2004089185 | 10/2004 |
| WO | 2004089186 | 10/2004 |
| WO | 2004089459 | 10/2004 |
| WO | 2004089460 | 10/2004 |
| WO | 2004090939 | 10/2004 |
| WO | 2004105861 | 12/2004 |
| WO | 2005096979 A1 | 10/2005 |
| WO | 2005096980 A1 | 10/2005 |
| WO | 2007030415 A2 | 9/2006 |
| WO | 2007041540 A1 | 4/2007 |
| WO | 2007046886 | 4/2007 |
| WO | 2007046886 A1 | 4/2007 |
| WO | 2007047122 A2 | 4/2007 |
| WO | 2008091983 A2 | 7/2008 |

OTHER PUBLICATIONS

European Patent Office, International Search Report issued in corresponding PCT Application serial No. PCT/US2008/069647 dated Oct. 6, 2008.

European Patent Office, International Search Report issued in corresponding PCT Application serial No. PCT/US2008/051868 dated Jul. 3, 2008.

European Patent Office, International Search Report issued in corresponding PCT Application serial No. PCT/US2008/051868 dated Sep. 4, 2008.

European Patent Office, International Search Report issued in corresponding PCT Application serial No. PCT/US2006/038536 dated Jan. 23, 2007.

Weber et al, "Treatment Apparatus and Methods for Inducing Microburn Patterns in Tissue", U.S. Appl. No. 12/019,874, filed Jan. 25, 2008.

Burns et al, "Treatment Apparatus and Methods for Delivering High Frequency Energy Across Large Tissue Areas", U.S. Appl. No. 12/171,010, filed Jul. 10, 2008.

European Patent Office, International Search Report issued in corresponding PCT Application serial No. PCT/US2006/038894 dated May 31, 2007.

Richard Wyeth et al, Electrode Assembly and Handpiece with Adjustable System Impedance, and Methods of Operating an Energy-Based Medical System to Treat Tissue, U.S. Appl. No. 11/537,155, filed Sep. 29, 2006.

European Patent Office, International Search Report issued in corresponding PCT Application serial No. PCT/US2006/022586 dated Dec. 1, 2006.

(56) References Cited

OTHER PUBLICATIONS

USPTO, Notice of Allowance issued in related U.S. Appl. No. 11/537,155 dated Apr. 25, 2011.
USPTO, Notice of Allowance issued in related U.S. Appl. No. 12/171,010 dated Apr. 13, 2012.
USPTO, Office Action issued in related U.S. Appl. No. 11/537,155 dated Nov. 16, 2010.
USPTO, Office Action issued in related U.S. Appl. No. 12/171,010 dated Oct. 6, 2011.
USPTO, final Office Action issued in related U.S. Appl. No. 12/019,874 dated Oct. 6, 2011.
USPTO, Office Action issued in related U.S. Appl. No. 12/019,874 dated May 5, 2011.
USPTO, final Office Action issued in related U.S. Appl. No. 11/470,041 dated Dec. 8, 2011.
USPTO, Office Action issued in related U.S. Appl. No. 11/470,041 dated May 26, 2011.
USPTO, Office Action issued in related U.S. Appl. No. 12/019,874 dated Apr. 5, 2012.
USPTO, final Office Action issued in related U.S. Appl. No. 12/019,874 dated Sep. 6, 2012.

\* cited by examiner

FIG. 8

TREATMENT APPARATUS AND METHODS FOR DELIVERING ENERGY AT MULTIPLE SELECTABLE DEPTHS IN TISSUE

CROSS-REFERENCE TO RELATED APPLICATIONS

This application claims the benefit of U.S. Provisional Application No. 60/728,339 filed Oct. 19, 2005, the disclosure of which is hereby incorporated by reference herein in its entirety.

FIELD OF THE INVENTION

The invention generally relates to apparatus and methods for treating tissue with high frequency energy and, more particularly, relates to apparatus and methods for delivering high frequency energy at multiple selectable depths into tissue.

BACKGROUND OF THE INVENTION

Devices that can treat tissue non-invasively are extensively used to treat numerous diverse skin conditions. Among skin treatment applications, non-invasive energy delivery devices may be used to tighten loose skin for making a patient appear younger, to remove skin spots or hair, or to kill bacteria. Such energy delivery devices emit electromagnetic energy with wavelengths distributed across the breadth of the electromagnetic spectrum, and include ultraviolet, visible, and infrared light, both incoherent and coherent; microwave and radiofrequency (RF) energy; as well as sonic and mechanical energy sources.

In particular, high frequency energy delivery devices may be used to treat skin tissue non-ablatively and non-invasively by passing high frequency energy through a surface of the skin. The high frequency energy heats tissue beneath the epidermis to a temperature sufficient to denature collagen, which is believed to cause the collagen to contract and shrink and, thereby, tighten the tissue. The skin is actively cooled to prevent damage to a skin epidermis layer proximate to a treatment tip of the device. Treatment with high frequency energy may also cause a mild inflammation in the tissue. The resultant inflammatory response of the tissue may cause new collagen to be generated over time, which increases tissue contraction.

Conventional treatment tips used in conjunction with such high frequency energy delivery devices effectively distribute the high frequency energy for uniform delivery across a surface of the tip. The uniform energy delivery minimizes locally hot spots on the tip that could cause patient burns despite the use of active cooling. However, some tissue types respond best to treatment when heat is delivered deep into the tissue. Other tissue types respond best when heat is delivered at a shallower depth into the tissue. The depth and/or dose of energy may be controlled by changing the frequency, by adjusting the power of the high frequency generator powering the energy delivery device, or by adjusting the amount of tissue cooling. Although these adjustments may alter the treatment depth of the energy delivered to the tissue, each approach has certain disadvantages and drawbacks that limit their application.

The depth and/or dose of energy may also be controlled by switching treatment tips to change the characteristics of an emitted electric field that delivers the energy to the tissue. However, switching treatment tips is a time consuming and inconvenient approach for changing the treatment depth. Moreover, switching treatment tips significantly increases treatment costs because a clinician must purchase and stock multiple different treatment tips each capable of emitting a different electric field for changing the treatment depth.

What is needed, therefore, are apparatus and methods for overcoming these and other disadvantages of conventional apparatus and methods for selectively adjusting the depth at which high frequency energy is delivered into tissue during non-invasive tissue treatments.

SUMMARY OF THE INVENTION

The invention is generally directed to treatment apparatus and methods for providing a selectable adjustable or variable depth of energy delivery into tissue during non-invasive tissue treatments. In accordance with one embodiment of the invention, the treatment apparatus includes an electrode assembly or structure that is positionable adjacent to a patient's tissue to be treated. The electrode structure includes at least first and second electrodes that are electrically isolated from each other. Electrical connections are coupled to the first and second electrodes. The electrical connections are configured to allow the first electrode to be selected for energizing to deliver energy at a first depth in the tissue and to allow the second electrode to be selected for energizing to deliver energy at a second depth in the tissue different from the first depth. Optionally, the electrical connections may be configured to allow both the first and second electrodes to be selected for energizing to deliver energy at a third depth in the tissue different from the first and second delivery depths.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

DETAILED DESCRIPTION

Figure 1:
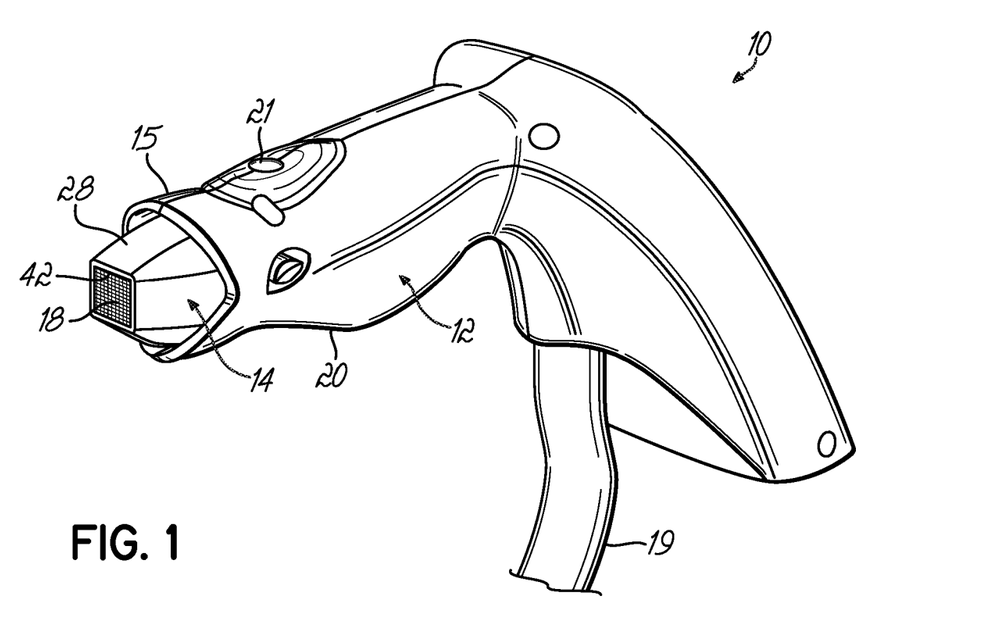
FIG. 1 is a perspective view of a handpiece including an electrode assembly in accordance with an embodiment of the invention.

With reference to FIG. 1, a treatment apparatus or handpiece 10 includes a housing 12 and an electrode structure or assembly 14 supported by the housing 12. Although the electrode assembly 14 is constituted by multiple components, the assembled components are understood to comprise a structure that is releasably coupled as a unit with the housing 12. Housing 12 may comprise a polymer or plastic material that is molded, such as by an injection molding process, into a three-dimensional shape. A portion of the electrode assembly 14 protrudes from a shroud 15 defined at one end of the housing 12 such that an electrode array 18 is exposed and visible when the electrode assembly 14 is coupled mechanically with the housing 12.

Figure 3:
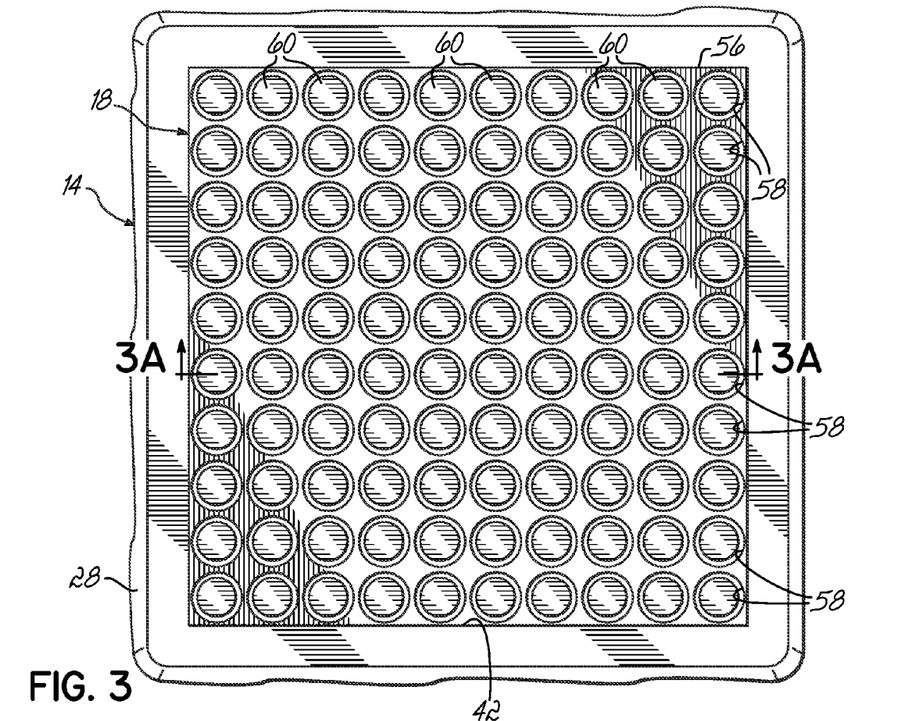
FIG. 3 is an end view of the electrode assembly of FIG. 1 in accordance with an embodiment of the invention and in which a dielectric layer supplying electrical insulation for the electrode array has been omitted for clarity of description.
Figure 3A:
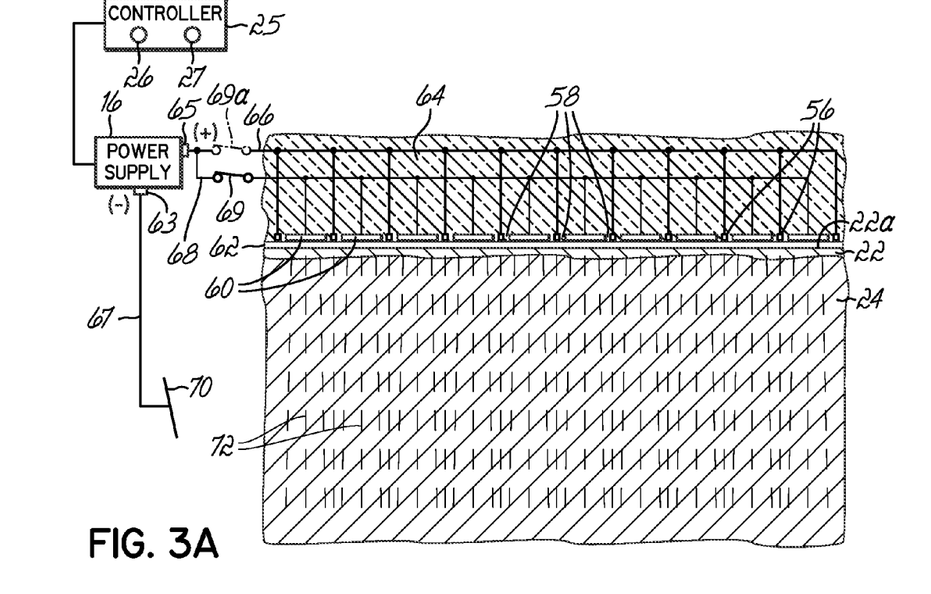
FIG. 3A is a diagrammatic cross-sectional view taken generally along line 3A-3A of FIG. 3 in which the electrode array is depicted as operating in a monopolar mode.

The housing 12 defines an inner cavity that houses electrical connections, which are discussed below, that electrically couple the electrode assembly 14 with an energy delivery source such as a high frequency energy source or power supply 16 (FIG. 3A). The high frequency power supply 16 supplies high frequency energy or voltage to one or more active electrodes 56, 60 (FIG. 3) carried by electrode assembly 14, which energize the active electrodes 56, 60 to deliver high frequency energy to a patient's tissue 24 (FIG. 3A). Housing 12 provides a suitable internal interface for connection to an electrical connecting cable 19 with insulated and shielded conductors or wires (not shown) that electrically couple the electrode assembly 14 with high frequency power supply 16.

A smoothly contoured grip portion 20 of handpiece 10 has a shape suitable for gripping and handling by the clinician. An exposed activation button 21 is accessible from the exterior of the gripped handpiece 10 to be depressed and released for controlling the delivery of high frequency energy from the electrode array 18. The grip portion 20 is adapted to be grasped by at least one hand of the clinician for manipulating the handpiece 10 to place the electrode assembly 14 to a location adjacent to a patient's skin 22 (FIG. 3A) and the underlying target tissue 24. Preferably, the electrode array 18 of electrode assembly 14 is in contact with an epidermis surface 22a of the skin 22. When the activation button 21 is depressed, high frequency electromagnetic energy radiated from the electrode array 18 is transferred to the target tissue 24.

A circuit (not shown) in the high frequency power supply 16 is operative to generate high frequency electrical current, typically in the radio-frequency (RF) region of the electromagnetic spectrum, which is transferred to at least the active electrodes of the electrode array 18. The operating frequency of power supply 16 may advantageously be in the range of several hundred kHz to about 20 MHz to impart a therapeutic effect to the tissue 24. The circuit of power supply 16 converts a line voltage into drive signals having an energy content and duty cycle appropriate for the amount of power and the mode of operation that have been selected by the clinician, as understood by a person having ordinary skill in the art.

A controller 25 has user input devices in the form of controls 26, 27 that may be used, for example, to adjust the applied voltage level to the electrode array 18 and to switch the electrode array 18 between different modes of operation, including but not limited to monopolar, bipolar, and tripolar modes of operation. The controller 25 includes a processor, which may be any suitable conventional microprocessor, microcontroller or digital signal processor, that controls and supervises the operation of the high frequency power supply 16 for regulating the power delivered from the power supply 16 to the electrode assembly 14. Controller 25, which may include a nonvolatile memory (not shown) storing programmed instructions or data for the processor, may be optionally integrated into the power supply 16.

Figure 2:
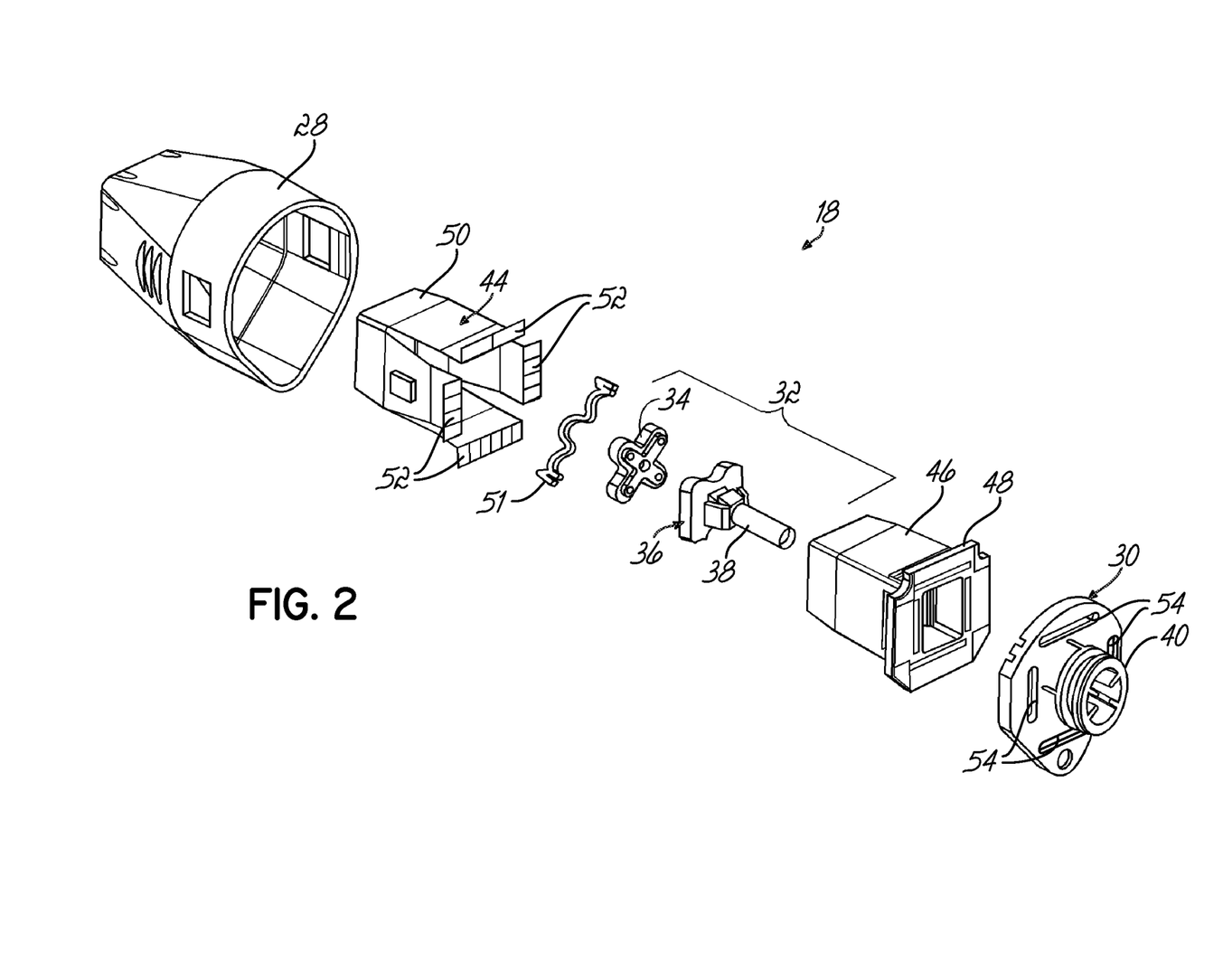
FIG. 2 is an exploded view of the electrode assembly of FIG. 1.

With reference to FIGS. 1 and 2, the electrode assembly 14 includes an outer shell 28 and a nipple 30 that is coupled with the open rearward end of the outer shell 28 to close an interior cavity. A fluid delivery member 32 is configured to direct coolant from a nozzle 34 to the backside of the electrode array 18 for controlling the temperature of the electrode array 18. Extending rearwardly from a central fluid coupling member 36 is a conduit 38 having a lumen defining a fluid path that conveys a flow of the coolant to the nozzle 34. The coolant is pumped from a coolant supply (not shown) through tubing that is mechanically coupled with a fitting 40 formed on the nipple 30 and hydraulically coupled with the lumen of the conduit 38.

The electrode array 18 is exposed through a window 42 defined in a forward open end of the outer shell 28. The electrode array 18 is illustrated as formed on a flexible sheet or substrate 44 of material wrapped about a forward end of a support member 46. The rearward end of the support member 46 includes a flange 48 used to couple the support member 46 to the nipple 30. The flexible substrate 44 may comprise a thin base polymer (e.g., polyimide) film 50 and thin conductive (e.g., copper) traces or leads 52 isolated electrically from each other by small intervening gaps. Flexible substrate 44 may comprise a flex circuit having a patterned conductive (i.e., copper) foil laminated to the base polymer (or other non-conductive material) film 50 or patterned conductive (i.e., copper) metallization layers directly deposited on the base polymer film 50 by, for example, a vacuum deposition technique, such as sputter deposition. Flex circuits, which are commonly used for flexible and high-density electronic interconnection applications, have a construction understood by a person having ordinary skill in the art.

A support member 51 bridges the window 42 for lending mechanical support to the flexible substrate 44. The substrate 44 is wrapped about the support member 46 such that the conductive leads 52 are exposed through slots 54 arranged about the periphery of the nipple 30. The conductive leads 52 are used to electrically couple the electrode array 18 with the high frequency power supply 16. The conductive leads 52 may also be used to couple other structures, such as impedance, pressure or thermal sensors (not shown), with the processor of the power supply 16 or another control element either inside the housing 12 or external to the housing 12.

With reference to FIGS. 3 and 3A and in accordance with one embodiment of the invention, the electrode array 18 comprises a conductive sheet electrode 56 including an array of voids 58 and a plurality of secondary electrodes 60 each positioned in a corresponding one of the voids 58. The voids 58 and secondary electrodes 60 are arranged in a matrix of rows and columns within the peripheral boundary of the sheet electrode 56, although the invention is not so limited. The sheet electrode 56 and secondary electrodes 60 are each constituted by an electrically conductive material, such as a metal like copper, gold, silver, aluminum, alloys of these materials, and the like. The sheet electrode 56 and secondary electrodes 60 have a substantially flat planar interleaved structure.

A thin layer 64 of a dielectric material is interposed between the sheet electrode 56 and the secondary electrodes 60, and a dielectric layer 62, which can be the same material as layer 64, covers a patient facing side of the electrodes 56, 60. When the electrode array 18 is positioned proximate to the skin 22, the thin dielectric layer 62 defines a substantially planar tissue treatment surface that at least partially contacts the surface 22a of the skin 22. The secondary electrodes 60 are electrically insulated from the sheet electrode 56 by portions of the dielectric layer 64, which operates as an electrical insulator. Suitable dielectric materials for layer 62 and layer 64 include any ceramic, polymer, or glass having an appropriate dielectric constant and dielectric strength as understood by a person having ordinary skill in the art. The dielectric layer 62 may be in contact with the electrodes 56, 60.

The sheet electrode 56 and the secondary electrodes 60 of the electrode array 18 are arranged relative to the dielectric layer 62 to define a structure similar to an electrical capacitor (e.g., two conductors separated by a non-conductive insulator) when the electrodes 56, 60 are energized to treat tissue 24. One conductor of the electrical capacitor consists of the sheet electrode 56 and secondary electrodes 60, the second conductor is represented by the skin 22 or the tissue 24 being treated, and the dielectric layer 62 separating the two conductors constitutes the non-conductive insulator. This component arrangement is advantageous in that the current flow through the sheet electrode 56 and secondary electrodes 60 to the underlying skin 22 and tissue 24 is more uniform than if the dielectric layer 62 were omitted. The capacitive effect of dielectric layer 62 may be controlled through the selection of the thickness, surface area and dielectric constant of layer 62, as well as by controlling the frequency of the high frequency power supplied from power supply 16.

In one embodiment of the invention, the electrode array 18 may comprise conductive features formed on the surface of the flexible substrate 44. Alternatively, the electrode array 18 may be fabricated on a separate substrate (not shown), such as a ceramic substrate, bonded to the base polymer film 50, and electrically coupled with the conductive leads 52, or in another manner, with the high frequency power supply 16.

The sheet electrode 56 of the electrode array 18 is electrically coupled by a network of conductors or electrical connections 66 with a terminal 65 of the high frequency power supply 16 having a positive voltage polarity. The secondary electrodes 60 of the electrode array 18 are likewise electrically coupled by a network of conductors or electrical connections 68 with the positive voltage polarity terminal 65 of the high frequency power supply 16. The high frequency power supply 16 is adapted to selectively energize the sheet electrode 56 to deliver energy at a first depth to the tissue 24 and the secondary electrodes 60 to deliver energy at a second depth to the tissue 24 by manipulating the electrical connections 68. The electrical connections 66, 68 may be routed to the high frequency power supply 16 through the electrical connecting cable 19 (FIG. 1) and may include conductive leads 52 (FIG. 2).

Figure 3B:
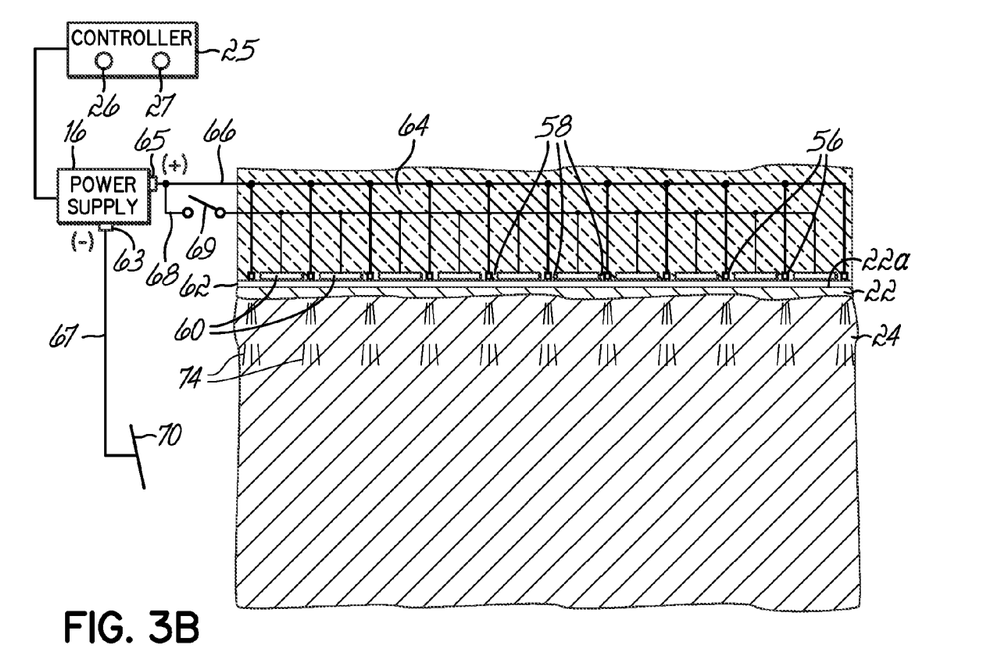
FIG. 3B is a diagrammatic cross-sectional view similar to FIG. 3A with the secondary electrodes in the electrode array not energized so that the depth of energy delivery is shallower than that delivered by the arrangement of FIG. 3A.

A switch 69, such as a relay or another type of switching device or circuit, that may be switched between opened and closed conditions to open and close, respectively, the signal path or circuit through the network of electrical connections 68 between the secondary electrodes 60 and the positive voltage polarity terminal 65 of the high frequency power supply 16. In the embodiment of FIGS. 3A, 3B, the sheet electrode 56 is electrically coupled by electrical connections 66 with the positive voltage polarity terminal 65 regardless of the setting or condition of switch 69. When switch 69 is closed, a first circuit is defined that electrically couples the sheet electrode 56 and the secondary electrodes 60 in parallel with the high frequency power supply 16. When switch 69 is open, a second circuit is defined that electrically couples only the sheet electrode 56 with the high frequency power supply 16. The switch 69 may be electrically coupled with the controller 25 so that, for example, one of the controls 26, 27 may be used to open and close the switch 69. The switch 69 may be integrated into the controller 25 or into the power supply 16, or may constitute a circuit element of the electrical connections 68 controlled by either the controller 25 or power supply 16.

The electrical connections 66, 68 may comprise multiple layers or levels of conductive traces or features in which each individual conductive feature layer is electrically isolated from adjacent levels with conductor-filled vias supplying electrical paths between levels or, alternatively, the electrical connections 66, 68 may comprise discrete conductors or wires. The electrical connections 66, 68 may comprise electrical contacts designed or adapted to be electrically coupled with the high frequency power supply 16.

A non-therapeutic passive or return electrode 70 is attached to a body surface of the patient, such as the patient's leg or back. The return electrode 70, which is not part of the housing 12 or electrode array 18, is positionable on the patient at a location remote or removed from the housing 12 and electrode array 18. The high frequency power supply 16 also includes another terminal 63 of opposite negative voltage polarity with which the return electrode 70 is electrically coupled by a signal path or electrical connection 67 to complete the circuit.

During a patient treatment procedure in which the electrode array 18 is energized in a monopolar mode of operation, high frequency current flows through the bulk of the patient between the sheet electrode 56 (and optionally secondary electrodes 60 if switch 69 is closed) and the return electrode 70. After collection by the return electrode 70, current is returned to the high frequency power supply 16 from the return electrode 70. Regardless of whether switch 69 is in an opened or closed state, the return electrode 70 and the negative voltage polarity terminal 63 of high frequency power supply 16 are connected. The return electrode 70 is non-therapeutic in that no significant heating is produced at its attachment site to the patient's body because of the low current density delivered across the relatively large surface area of the return electrode 70.

During operation and with reference to FIGS. 3A and 3B, switch 69 is employed to change the operation of the handpiece 10 to treat tissue 24 at two different depths. When switch 69 is closed to form a first circuit that includes secondary electrodes 60 as depicted in FIG. 3A, high frequency current is delivered over the network of electrical connections 68 from the positive voltage polarity terminal 65 of high frequency power supply 16 to the sheet electrode 56 and also to the secondary electrodes 60. High frequency energy 72 is delivered in a monopolar mode from the energized sheet electrode 56 and secondary electrodes 60 to the tissue 24. The sheet electrode 56 and secondary electrodes 60 operate as active electrodes that emit high frequency energy 72 that penetrates through the dielectric layer 62 and skin 22 and capacitively couples with the target tissue 24 beneath the skin 22 to generate a beneficial effect. The sheet electrode 56 and secondary electrodes 60 emulate a solid sheet of conductive material such that high frequency energy 72 is delivered to a relatively deep depth in the tissue 24 beneath the skin 22. In particular, when the electrode array 18 is energized with switch 69 closed, the high frequency energy 72 is delivered to a relatively deep first depth in the tissue 24 below the skin surface 22a.

With switch 69 opened to form a second circuit that omits secondary electrodes 60 as depicted in FIG. 3B, high frequency power or current is delivered over the network of electrical connections 66 from the positive voltage polarity terminal 65 of high frequency power supply 16 to only the sheet electrode 56. High frequency current is no longer delivered over the network of electrical connections 68 from the positive voltage polarity terminal 65 of high frequency power supply 16 to the secondary electrodes 60. In this instance, only the sheet electrode 56 operates as an active electrode and secondary electrodes 60 are deactivated and no longer energized. High frequency energy 74 is delivered from sheet electrode 56 to the tissue 24 by capacitive coupling through the dielectric layer 62 in a manner emulating a sheet of conductive material perforated by multiple voids 58. As a result, the high frequency energy 74 is delivered to a relatively shallow second depth into the tissue 24 beneath the skin 22 in comparison with the delivery depth of high frequency energy 72 (FIG. 3A).

The specific values of the two different depths of high frequency energy delivery are contingent upon multiple factors, such as the frequency and power of the high frequency power delivered to the electrode array 18, and the proportion of the area of the window 42 that is energized. The energy delivery depths may be measured as either average or peak depths relative to the skin surface 22a or interface between the skin 22 and tissue 24, or in a different relative manner. The result is that handpiece 10 furnishes a treatment apparatus having a selectable variable depth of energy delivery in tissue 24 of a patient. This ability to selectively control the delivery of high frequency energy from the secondary electrodes 60 in the electrode array 18 to the tissue 24 permits a single electrode assembly 14 to be used to generate different electromagnetic fields suitable for establishing different types and depths of heating profiles in the treated tissue 24 at any given power setting of the power supply 16.

The high frequency voltage difference between sheet electrode 56 and, optionally, secondary electrodes 60 and the return electrode 70 develops an electric field near the site of the target tissue 24 effective for transferring high frequency energy to tissue 24. The high frequency energy 72, 74 treats tissue 24 non-ablatively and non-invasively by passing or transferring high frequency energy 72, 74 through an epidermis surface of patient's skin 22 to the tissue 24, while actively cooling the skin 22 to prevent damage to the epidermis layer of skin 22. The return electrode 70 completes the current path between the sheet electrode 56 and, optionally, secondary electrodes 60 and the high frequency power supply 16.

The treatment depth may also be further adjustable by programming different output parameters for the high frequency power supplied from power supply 16. More specifically, various different high frequency currents and voltages may be supplied from the high frequency power supply 16 to the electrode array 18 with the switch 69 closed. As a result, multiple additional treatment depths may be achieved with a single electrode assembly 14 as the high frequency currents and voltages may be varied across a wide range of values.

In an alternative embodiment of the invention, another switch 69a (FIG. 3A) similar to switch 69 may be installed in the network of electrical connections 66 coupling the sheet electrode 56 with the high frequency power supply 16. When switch 69a is opened and switch 69 is closed, the secondary electrodes 60 could be used to deliver high frequency energy into the tissue 24 at yet a different depth while operating in a monopolar mode. In this instance, only the energized secondary electrodes 60 operate as active electrodes and sheet electrode 56 is deactivated and no longer energized or powered. The switch 69a may be integrated into the controller 25 or into the power supply 16, or may constitute a circuit element of the electrical connections 66 controlled by either the controller 25 or power supply 16.

Figures 3C, 4:
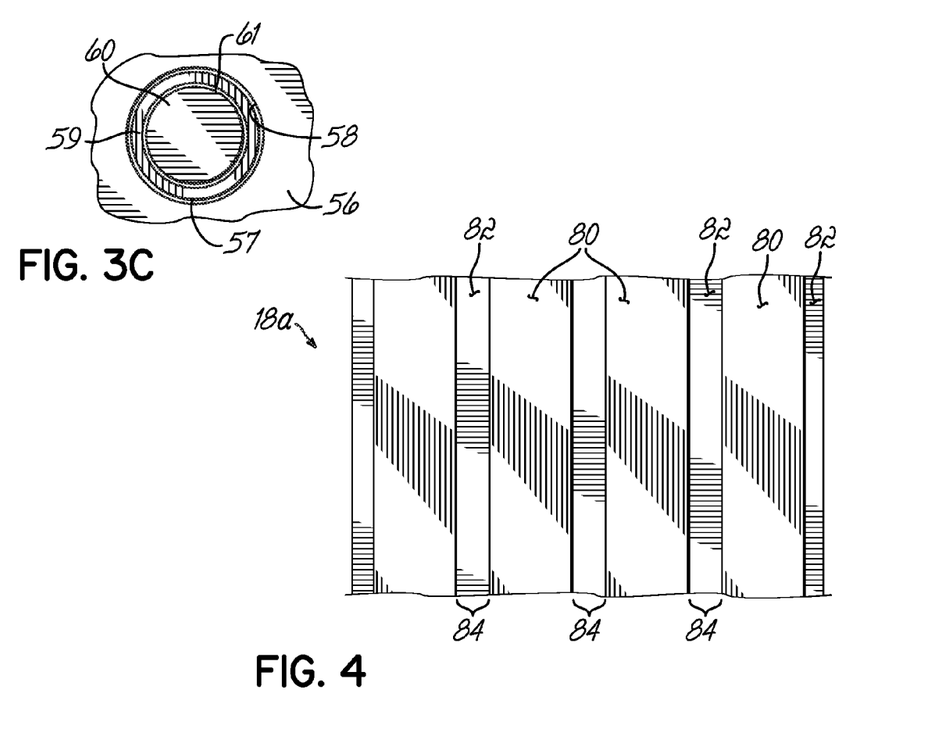
FIG. 3C is a view of a portion of an electrode assembly in accordance with an alternative embodiment of the present invention.
FIG. 4 is an end view of an electrode array for use in the electrode assembly of FIG. 1 in accordance with an alternative embodiment of the invention and shown with a dielectric layer removed for clarity.

With reference to FIG. 3C in which like reference numerals refer to like features in FIGS. 1-3 and in an alternative embodiment of the invention, the electrode array 18 of electrode assembly 14 (FIGS. 1, 2) may be supplied with another set of electrically isolated secondary electrodes 59 of which only a single secondary electrode 59 is visible in FIG. 3C. Each of the secondary electrodes 59 is disposed within a corresponding one of the voids 58 in sheet electrode 56 along with one of the secondary electrodes 60. Each secondary electrode 59 is separated from its corresponding secondary electrode 60 by an annular dielectric-filled gap 61 and from the edge of sheet electrode 56 defined about void 58 by another annular dielectric-filled gap 57. The dielectric-filled gaps 57, 61 electrically isolate the secondary electrodes 59 from the sheet electrode 56 and the secondary electrodes 60.

An independent network of electrical connections (not shown), similar to electrical connections 66, 68, couple the additional secondary electrodes 59 through another switch (not shown), similar to switches 69, 69a, with the positive voltage polarity terminal 65 of the high frequency power supply 16. Selecting from among possible combinations of the different sets of electrodes to emit high frequency energy permits the treatment depth to be varied. For example, if the high frequency RMS voltage is kept constant, high frequency energy delivered from sheet electrode 56 alone to the tissue 24 will result in a relatively shallow delivery depth. Energizing secondary electrodes 60, in addition to sheet electrode 56, at a constant high frequency RMS voltage will increase the energy delivery depth, as the effective area of the voids 58 in sheet electrode 56 is incrementally decreased. Energizing secondary electrodes 59 and secondary electrodes 60, in addition to sheet electrode 56, at a constant high frequency RMS voltage will further increase the energy delivery depth. Alternatively, the high frequency voltage supplied to one of the sets of secondary electrodes 59, 60 may be attenuated using passive components, such as capacitors, inductors or resistors, which may be switched into and out of the circuit using relays. The invention contemplates that the electrode array 18 may include more than two sets of secondary electrodes 59, 60 for increasing the number of possible energy delivery depths.

Figure 5:
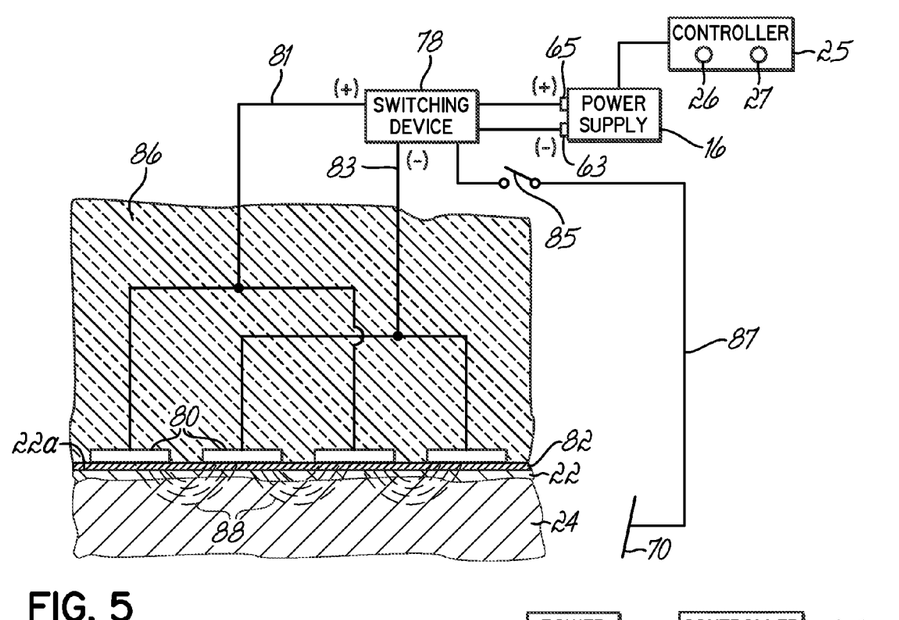
FIG. 5 is a diagrammatic cross-sectional view of the electrode array of FIG. 4 in which the electrode array of FIG. 4 is operating in a bipolar mode.
Figure 6:
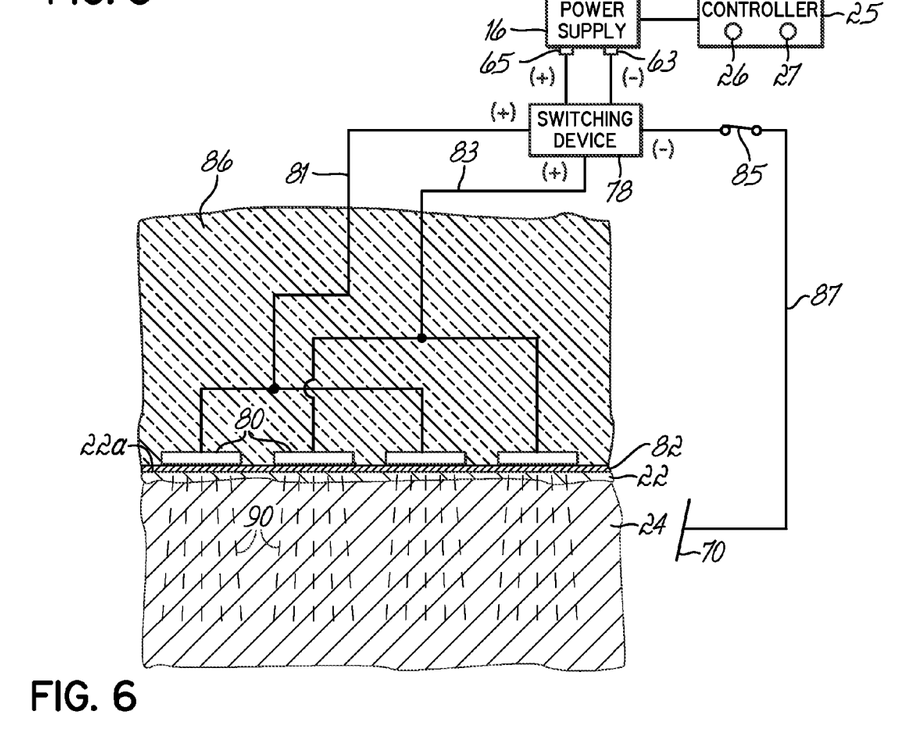
FIG. 6 is a diagrammatic cross-sectional view similar to FIG. 5 in which the electrode array of FIG. 4 is operating in a monopolar mode.

With reference to FIGS. 4-6 in which like reference numerals refer to like features in FIGS. 1-3 and in accordance with an alternative embodiment of the invention, an electrode array 18a for use with handpiece 10 may have a configuration that permits a clinician to switch the electrode array 18a between a monopolar mode of energy delivery and a bipolar mode of energy delivery. Electrode array 18a includes a set of active electrodes 80 composed of a conductive material (e.g., copper) and a skin-contacting dielectric layer or substrate 82 on which the electrodes 80 are arranged. Adjacent active electrodes 80 are separated from each other by gaps 84 that are non-conductive. To ensure electrical isolation and prevent shorting between adjacent active electrodes 80 and with nearby conductive structures inside the housing 12 (FIG. 1), a layer 86 (FIG. 5) of a dielectric material fills the volume between and around the active electrodes 80. The active electrodes 80 have a parallel arrangement on the dielectric substrate 82, although the invention is not so limited.

The invention contemplates that the active electrodes 80 may have different geometries and arrangements than depicted in the exemplary embodiment of FIG. 4.

With reference to FIG. 5, the active electrodes 80 may be electrically coupled with the high frequency power supply 16 such that the electrode array 18a operates in a bipolar mode. Specifically, the polarity of the active electrodes 80 is alternated such that any two adjacent electrodes 80 have opposite polarities. As a result, return electrode 70 is not required on the patient to complete the current path with the high frequency power supply 16. To achieve bipolar operation, every other active electrode 80 is coupled by a network of conductors or electrical connections 81 with the positive polarity voltage terminal 65 of the high frequency power supply 16 and intervening active electrodes 80 are coupled by a network of conductors or electrical connections 83 with the negative polarity voltage terminal 63 of the high frequency power supply 16. When the active electrodes 80 are operating in bipolar mode, the return electrode 70 does not participate in the circuit and, therefore, is not coupled electrically with the high frequency power supply 16. To that end, a switch 85, such as a relay or another type of switching device or circuit, is switched to an open condition to open a signal path or electrical connection 87 between the negative voltage polarity terminal 63 of the high frequency power supply 16 and the return electrode 70. Switch 85 may be integrated into the controller 25 or into the power supply 16, or may constitute a circuit element of the electrical connection 87 controlled by either the controller 25 or power supply 16.

High frequency energy 88 is delivered from active electrodes 80 by capacitive coupling through the dielectric substrate 82 and through the skin 22 to a relatively shallow depth in tissue 24. The return current path to the high frequency power supply 16 does not pass through the bulk of the patient. Instead, a fraction of the active electrodes 80 operate to deliver high frequency energy 88 and another fraction of the active electrodes 80 supply the return current path so that the delivery and return subsets of the electrodes 80 are both therapeutic.

With reference to FIG. 6, the same set of active electrodes 80 may be electrically coupled with the high frequency power supply 16 such that the electrode array 18 operates in a monopolar mode. Specifically, all active electrodes 80 are coupled electrically by the electrical connections 81, 83 with the positive polarity voltage terminal 63 of the high frequency power supply 16. Switch 85, is switched to a closed condition to close the electrical connection 87 between the negative voltage polarity terminal 63 of the high frequency power supply 16 and the return electrode 70. High frequency energy 90 is delivered by capacitive coupling through the dielectric substrate 82 and through the skin 22 to a relatively deep depth in tissue 24, as compared with operation in bipolar mode (FIG. 5).

A switching device or circuit 78 may be included for switching the operation of the active electrodes 80 between the bipolar mode (FIG. 5) and the monopolar mode (FIG. 6) by reconfiguring the electrical connections 81, 83 in order to change the depth of the delivered energy into the tissue 24. The switching circuit 78, which may include one or more individual switches, may be switched to change the signal path for the high frequency energy under the control of controller 25. The switching circuit 78 configures the terminal connections for the networks of electrical connections 81, 83, 87 with the power supply 16 by making and breaking electrical connections that define the signal paths to the terminals 63, 65. The switching circuit 78 has at least first and second conditions for the signal paths from the terminals 63, 65 of the power supply 16 to switch the active electrodes 80 between bipolar and monopolar modes of operation. The switching circuit 78 may be integrated into the controller 25 or into the power supply 16, or may constitute a circuit element of the electrical connections 81, 83, 87 controlled by either the controller 25 or power supply 16. The electrical connections 81, 83 may be routed to the high frequency power supply 16 through the electrical connecting cable 19 (FIG. 1) and may include conductive leads 52 (FIG. 2).

The switched operation of the handpiece 10 furnishes a treatment apparatus having a selectable variable depth for delivering energy into tissue 24 of a patient that depends upon the condition of the switching circuit 78 to create either a monopolar operational mode or a bipolar operational mode. High frequency energy 88 (FIG. 5) is delivered at a shallower depth into the tissue 24, in comparison to high frequency energy 90 (FIG. 6), when the handpiece 10 is operating in the bipolar mode.

Figures 7, 8:
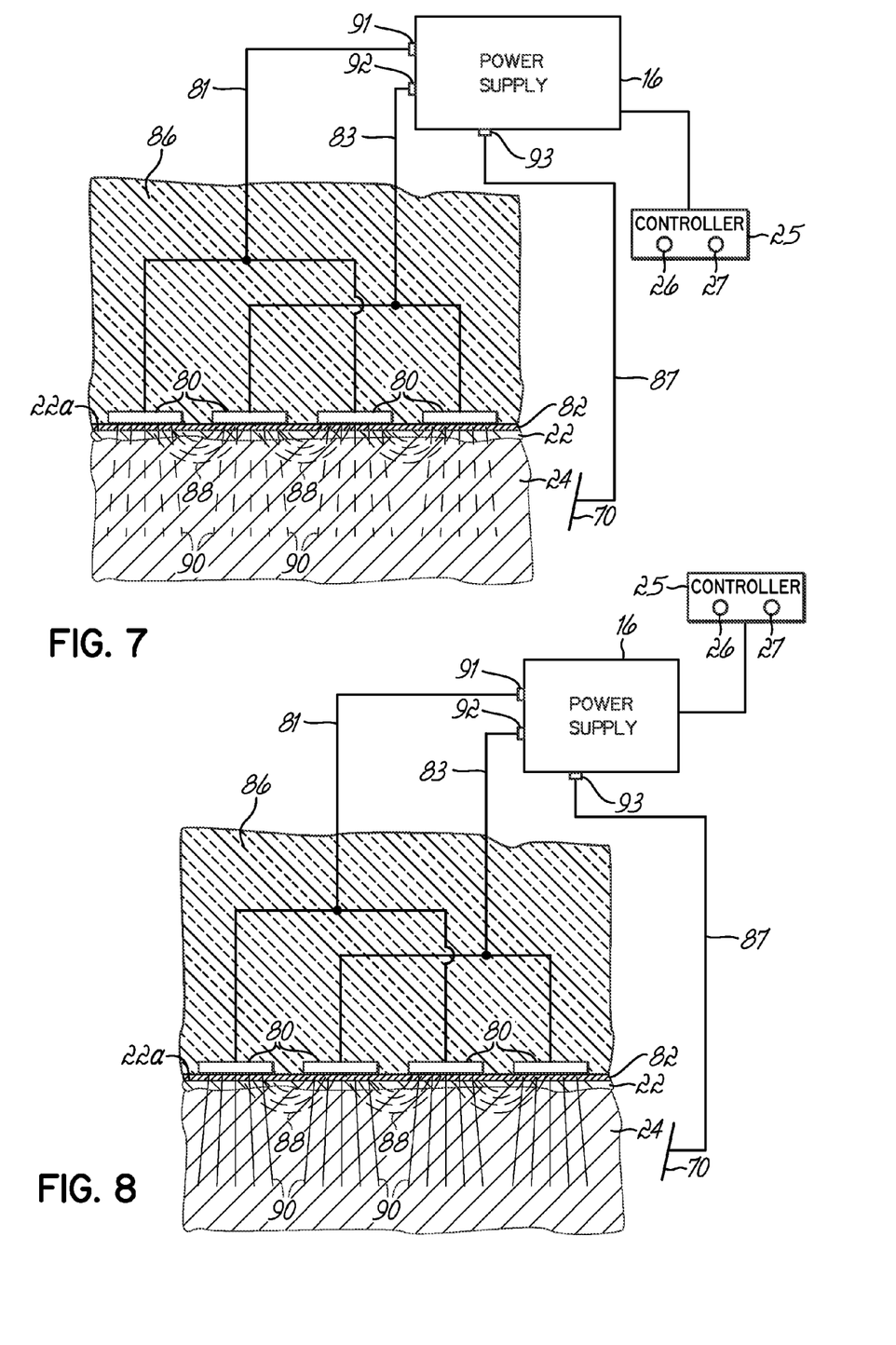
FIG. 7 is a diagrammatic cross-sectional view similar to FIG. 6 depicting the electrode array of FIG. 4 operating in a tripolar mode with a predominant bipolar component.
FIG. 8 is a diagrammatic cross-sectional view similar to FIG. 7 depicting the electrode array of FIG. 4 operating in a tripolar mode with a predominant monopolar component.

With reference to FIG. 7, the circuitry of the high frequency power supply 16 may be configured with three voltage terminals 91, 92, 93 of different polarity that operate at the same frequency but at different phase angles. The polarity of the active electrodes 80 is alternated such that any two adjacent electrodes 80 are driven with different phase angles. In addition, the return electrode 70 is driven with a phase angle that differs from the phase angles of the active electrodes 80. In this embodiment of the invention, energy is concurrently delivered to tissue 24 in bipolar and monopolar modes. Power supply 16 controls the phase angle of the power delivered to the electrodes 70, 80 so that energy flows as desired between the active electrodes 80 and also between the active electrodes 80 and the return electrode 70.

For example, half of the active electrodes 80 coupled with one voltage terminal 92 may be driven 180° out of phase with the other half of the active electrodes 80 coupled with a different voltage terminal 91. The return electrode 70, which is coupled with the third voltage terminal 93, may be driven at −90° out of phase with half of the active electrodes 80 and at +90° out of phase with the other half of the active electrodes 80. Although not wishing to be bound by theory, this is believed to result in a "tripolar" mode of operation consisting of a component mixture that includes a predominant bipolar component that delivers high frequency energy 88 at a relatively shallow depth in the tissue 24 and a minor monopolar component that delivers high frequency energy 90 at a significantly deeper depth into the tissue 24. The strength of the bipolar component is controlled by the magnitude of the phase angle separation between the three voltage terminals 91, 92, 93. On average, the high frequency energy 88, 90 is delivered into tissue 24 at a relatively shallow depth.

With reference to FIG. 8, the individual phase angles may be changed such that the monopolar mode dominates over the bipolar mode for deeper delivery of high frequency energy 88, 90 to the tissue 24. For example, half of the active electrodes 80 coupled with one voltage terminal 93 may be driven 40° out of phase with the other half of the active electrodes 80 coupled with a different voltage terminal 91. The return electrode 70, which is coupled with the third voltage terminal 92, may be driven at −160° out of phase with half of the active electrodes 80 and at −200° out of phase with the other half of the active electrodes 80. Although not wishing to be bound by theory, this is believed to result in a different "tripolar" mode of operation consisting of a component mixture that includes a significant monopolar component that delivers high frequency energy 90 at a relatively deep depth in the tissue 24 and a lesser bipolar component that delivers high frequency energy 88 at a significantly shallower depth into the tissue 24.

On average, the delivery depth for the high frequency energy 88, 90 increases when operating with the set of phase angles in FIG. 8 as opposed to the set of phase angles in FIG. 7.

The selection of the individual phase angles furnishes a treatment apparatus having a selectable variable depth for delivering energy into tissue 24 of a patient.

In yet another alternative embodiment of the invention, the active electrodes 80 and return electrode 70 may be operated in a duty cycle mode in which the electrode array 18a operates in monopolar mode (FIG. 6) for a fraction of the total treatment time and operates in bipolar mode (FIG. 5) for the remainder of the total treatment time. The power supply 16 may be switched between monopolar and bipolar modes to provide the duty cycle mode using semiconductor switches or the like. The switching between monopolar and bipolar modes may occur at a frequency greater than about one Hz, and optionally as high as several hundred Hz.

The circuit or circuitry in the controller 25 may be configured to cause the high frequency power supply 16 to energize the electrodes 70, 80 in either a monopolar, bipolar, or tripolar mode, contingent upon a depth of energy delivery desired by a clinician. The controller 25 may include clinician mode setting control 26 separate from a power control 27 for changing which electrodes 70, 80 are energized to change a depth of energy delivered. Clinician setting control 26, which is separate from the power control 27, varies the monopolar/bipolar mode of operation of the electrodes 70, 80 for changing the depth of energy delivery into the tissue 24. Any number of different setting levels for clinician setting control 26 can be provided using digital or analog control circuits. For example, as few as two or three levels may be set using control 26, or as many as ten, fifty, one hundred, or several hundred levels may be set using control 26.

Handpiece 10 may be used to deliver high frequency energy to modify tissue 24 including, but not limited to, collagen-containing tissue, in the epidermal, dermal and subcutaneous tissue layers, including adipose tissue. The modification of the tissue 24 may comprise altering a physical feature of the tissue 24, a structure of the tissue 24, or a physical property of the tissue 24. The tissue modification may be achieved by delivering sufficient energy to modify collagen containing tissue, cause collagen shrinkage, and/or a wound healing response including the deposition of new or nascent collagen, and the like.

Handpiece 10 may be utilized for performing a number of treatments of the skin 22 and underlying tissue 24 including but not limited to, dermal remodeling and tightening, wrinkle reduction, elastosis reduction, scar reduction, acne treatment, sebaceous gland removal/deactivation and reduction of activity of sebaceous gland, hair follicle removal, adipose tissue remodeling/removal, spider vein removal, modification of contour irregularities of a skin surface, creation of scar or nascent collagen, reduction of bacteria activity of skin, reduction of skin pore size, unclogging skin pores, and the like. Various treatments suitable for high frequency energy delivering devices, and various optimal structures for providing such energy and for actively cooling the skin 22 to minimize any damage to surface skin 22 or tissue 24, are disclosed in commonly-assigned U.S. Pat. Nos. 5,660,836, 6,350,276, and 6,425,912, the disclosure of each of which is hereby incorporated by reference herein in its entirety.

The electrode assemblies 14 of the invention may be used to estimate local impedance factors, as disclosed in application Ser. No. 11/470,041, filed on Sep. 5, 2006 and entitled "Method and Apparatus for Estimating a Local Impedance Factor"; the disclosure of the referenced application is hereby incorporated by reference herein in its entirety.

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. A treatment method for delivering energy at a selectable variable depth into tissue of a patient, the energy being delivered with an electrode array including a sheet electrode with a plurality of voids and a plurality of secondary electrodes each positioned in a corresponding one of the voids, the sheet electrode and the secondary electrodes separated from a surface of the tissue by a first dielectric layer, and the voids and the secondary electrodes are arranged in a matrix of rows and columns within the sheet electrode, the treatment method comprising:

electrically connecting the sheet electrode and the secondary electrodes with a high frequency power supply to form a first circuit in which the sheet electrode and the secondary electrodes emulate a solid sheet of a conductive material;

non-invasively delivering energy from the sheet electrode and the secondary electrodes in the first circuit and through the first dielectric layer into the tissue at a first average depth relative to the surface of the tissue, wherein the energy from the secondary electrodes is delivered in a pattern determined by the matrix of rows and columns;

reconfiguring the electrical connections of the sheet electrode and the secondary electrodes to disconnect the secondary electrodes from the high frequency power supply and form a second circuit in which the sheet electrode emulates a perforated sheet of the conductive material; and non-invasively delivering energy from the sheet electrode in the second circuit and through the first dielectric layer into the tissue at a second average depth relative to the skin surface.

2. The treatment method of claim 1 wherein the non-invasively delivering energy at the first average depth comprises:

capacitively coupling energy to the tissue to deliver the energy at the first average depth.

3. The treatment method of claim 1 wherein the electrically connecting the conductive sheet electrode and the secondary electrodes with the power supply to form the first circuit further comprises:

electrically connecting a return electrode with a first terminal of the high frequency power supply; and electrically connecting the sheet electrode and the secondary electrodes with a second terminal of the high frequency power supply.

4. The treatment method of claim 1 further comprising:

reconfiguring the electrical connections of the sheet electrode and the secondary electrodes to disconnect the sheet electrode from the high frequency power supply and form a third circuit in which only the secondary electrodes are coupled with the high frequency power supply; and non-invasively delivering energy from the secondary electrodes in the third circuit into the tissue at a third average depth relative to the skin surface.

5. The treatment method of claim 1 wherein the non-invasively delivering energy from the sheet electrode and the secondary electrodes in the first circuit and through the dielectric layer into the tissue at a first average depth relative to the surface of the tissue comprises:
delivering the energy from the secondary electrodes through a second dielectric layer interposed between the sheet electrode and the secondary electrodes.

6. The treatment method of claim 1 wherein each of the voids in the sheet electrode is occupied by one of the secondary electrodes.

* * * * *